(12) United States Patent
Motte et al.

(10) Patent No.: US 11,432,567 B2
(45) Date of Patent: Sep. 6, 2022

(54) INSECT POWDER FOR THE PREVENTION OR REDUCTION OF STRESS IN FISH DURING REARING

(71) Applicant: YNSECT, Evry (FR)

(72) Inventors: Constant Motte, Hem (FR); Benjamin Armenjon, Paris (FR)

(73) Assignee: YNSECT, Évry-Courcouronnes (FR)

( * ) Notice: Subject to any disclaimer, the term of this patent is extended or adjusted under 35 U.S.C. 154(b) by 312 days.

(21) Appl. No.: 16/641,806

(22) PCT Filed: Sep. 5, 2018

(86) PCT No.: PCT/FR2018/052166
§ 371 (c)(1),
(2) Date: Feb. 25, 2020

(87) PCT Pub. No.: WO2019/048776
PCT Pub. Date: Mar. 14, 2019

(65) Prior Publication Data
US 2020/0214318 A1      Jul. 9, 2020

(30) Foreign Application Priority Data

Sep. 6, 2017   (FR) ...................................... 1758220

(51) Int. Cl.
| | | |
|---|---|---|
| *A61K 35/60* | (2006.01) | |
| *A23K 10/20* | (2016.01) | |
| *A23K 50/80* | (2016.01) | |
| *A61K 35/64* | (2015.01) | |

(52) U.S. Cl.
CPC .............. *A23K 10/20* (2016.05); *A23K 50/80* (2016.05); *A61K 35/64* (2013.01)

(58) Field of Classification Search
CPC ................................ A23K 50/80; A61K 35/64
See application file for complete search history.

(56) References Cited

U.S. PATENT DOCUMENTS

2018/0303126 A1   10/2018   Hubert et al.

FOREIGN PATENT DOCUMENTS

| CN | 101856072 A | * | 10/2010 | |
|---|---|---|---|---|
| CN | 105831485 A | | 8/2016 | |
| WO | 9834498 A1 | | 8/1998 | |
| WO | 2009140327 A2 | | 11/2009 | |
| WO | 2015118253 A1 | | 8/2015 | |
| WO | WO-2016108037 A1 | * | 7/2016 | ............. A23K 10/20 |
| WO | 2017068278 A1 | | 4/2017 | |

OTHER PUBLICATIONS

Finke, M. D., "Complete Nutrient Content of Four Species of Commercially Available Feeder Insects Fed Enhanced Diets During Growth", Zoo Biology, vol. 34, No. 6, pp. 554-564, Nov. 1, 2015, SP055532095.

International Search Report (PCT/ISA/210) dated Jan. 2, 2019, by the European Patent Office as the International Searching Authority for International Application No. PCT/FR2018/052166.

Sanchez-Muros, Ma J. et al., "Nutritional evaluation of *Tenebrio molitor* meal as fishmeal substitute for tilapia (*Oreochromis niloticus*) diet", Aquaculture Nutrition, vol. 22, No. 5, pp. 943-955, 2016, XP009505213.

Written Opinion (PCT/ISA/237) dated Jan. 2, 2019, by the European Patent Office as the International Searching Authority for International Application No. PCT/FR2018/052166.

* cited by examiner

*Primary Examiner* — Qiuwen Mi
(74) *Attorney, Agent, or Firm* — Panitch Schwarze Belisario & Nadel LLP; Erin M. Dunston

(57) ABSTRACT

The present invention relates to a powder made of insects, for use in the prevention or reduction of stress in fish being farmed.

9 Claims, 2 Drawing Sheets

INSECT POWDER FOR THE PREVENTION OR REDUCTION OF STRESS IN FISH DURING REARING

Figure 1:
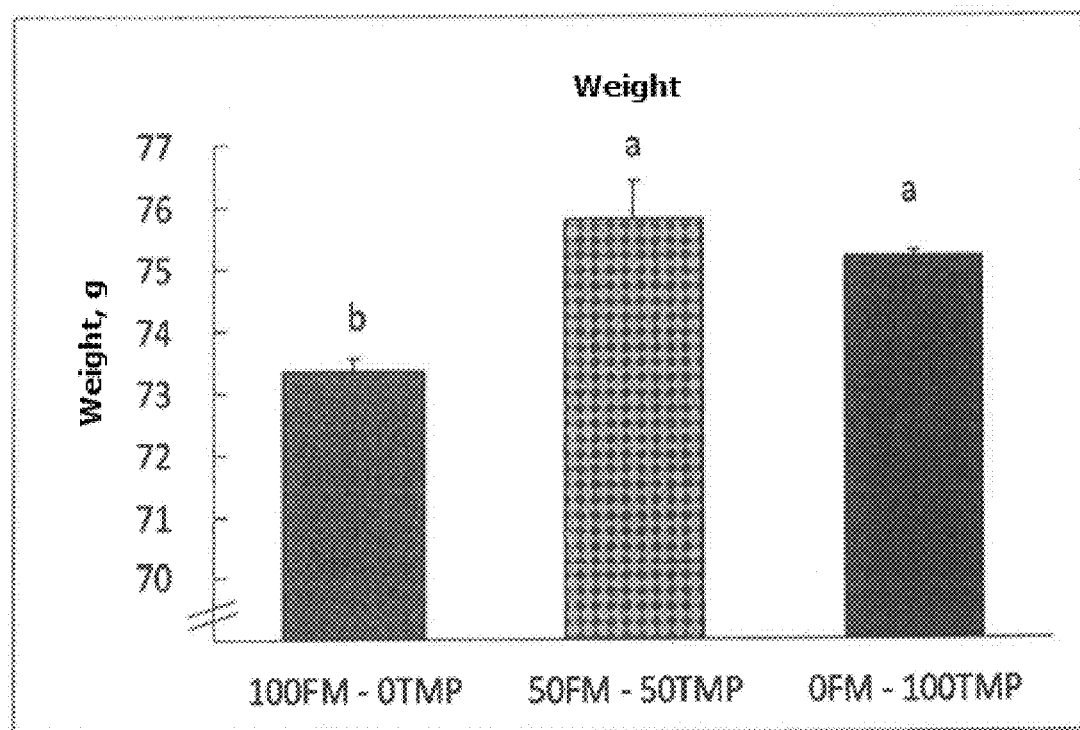

The invention relates to an insect powder for use thereof for the prevention or reduction of stress in fish during their rearing.

By "insect powder", is meant a composition, in the form of particles, prepared solely from insects and optionally water.

The residual moisture level in the insect powder is comprised between 2 and 15%, preferably between 5 and 10%, more preferentially between 4 and 8%. This moisture level can for example be determined according to the method originating from EC Regulation 152/2009 of 27 Jan. 2009 (103° C./4 h).

It will be noted that, in the context of the present application, and unless otherwise stipulated, the ranges of values indicated are to be understood as including boundaries.

Throughout the entire application, when no date is specified for a regulation, a standard or a directive, it is the regulation, standard or directive in force on the date of filing.

When the insect powder is ground to a particle size acceptable for human or animal nutrition, the latter can be referred to as "insect meal". By "particle size acceptable for human or animal nutrition" is meant a particle size comprised between 100 μm and 1.5 mm, preferentially comprised between 300 μm and 1 mm, more preferentially between 500 and 800 μm.

By "insects" is meant in particular Coleoptera, Diptera, Lepidoptera, Orthoptera, Hymenoptera, Dictyoptera, grouping together in particular the Blattoptera, including Isoptera, and the Mantoptera, Phasmoptera, Hemiptera, Heteroptera, Ephemeroptera and Mecoptera, or mixtures thereof, preferably Coleoptera.

Preferentially, the beetles belong to the families of the Tenebrionidae, Melolonthidae, Dermestidae, Coccinellidae, Cerambycidae, Carabidae, Buprestidae, Cetoniidae, Dryophthoridae, or mixtures thereof.

More preferentially, they are the following beetles: *Tenebrio molitor, Aiphitobius diaperinus, Zophobas morio, Tenebrio obscurus, Tribolium castaneum* and *Rhynchophorus ferrugineus*, or mixtures thereof, even more preferentially *Tenebrio molitor*.

The insect powder to which the invention relates is thus preferably a beetle powder, and more particularly, a powder of *Tenebrio molitor*.

Advantageously, the insect powder is obtained from the larval stage of the insect species mentioned above.

By "rearing" is meant the production then husbandry and growth of the fish, from the fry stage to the adult stage.

More particularly, the rearing to which the invention relates is rearing for commercial purposes, allowing the intensive production of fish, such as rearing in an enclosed space (tanks, fish pots or cages).

By "stress" is meant more particularly the stress due to handling (in particular handling known as "commercial condition handling") such as handling during the recovery of the fish from their enclosed space, during transfer from one enclosed space to another, during transfer to the factory for processing and killing, and during killing itself.

More particularly, the invention relates to an insect powder for use thereof for the prevention or reduction of stress in fish following (or resulting from) their transfer from fresh water to seawater or salt water during rearing.

The fish to which the invention relates are thus preferably all the fish that are intended to be transferred, during their rearing, from fresh water to seawater.

These fish are thus particularly the fish which, during their life cycle in the wild state, migrate from fresh water to seawater.

More particularly, the invention relates to fish which reproduce in fresh water, and undergo the main part of their growth in seawater. These fish are commonly called anadromous fish.

Advantageously, the insect powder is used, according to the invention, to prevent or reduce the stress, during rearing, of the fish belonging to the Salmonidae family.

Preferably, the fish belong to the genus *Salmo, Savelinus, Onchorynchus*, and/or *Hucho*, more preferentially *Salmo*.

The species particularly preferred according to the invention are: *Salmo salar* (Atlantic Salmon), *Salmo trutta* (Brown Trout or Common Trout), *Oncorhynchus kisutch* (Pacific Salmon), *Oncorhynchus tshawytscha* (King Salmon), *Onchorynchus mykiss* (Rainbow Trout) and *Salvelinus alpinus* (Arctic Char).

"Smoltification" denotes the set of physical and physiological processes (in particular metabolic), allowing fish originating from fresh water to adapt to the conditions of life in seawater.

In fact, following their transfer into seawater, the fish may be subjected to stress conditions, such as stress conditions due to the change of environment (salinity, nutrition regime, overpopulation) to which they must adapt. The intensity of the stress conditions may vary according to the implementation of the rearing. Mention may be made for example, of minimal stress conditions (experimental conditions comprising for example handling precautions) or, for more intense stress conditions, standard stress conditions of rearing.

However, some fish are not successful in adapting to these conditions, and they die.

This failure of adaptation or acclimatization of the fish to the conditions of life in seawater or salt water can thus be ameliorated by using an insect powder.

The invention therefore also relates to an insect powder for use thereof for the prevention or reduction of mortality in fish during their rearing.

More particularly, the invention relates to an insect powder for use thereof for the prevention or reduction of mortality in fish following (or resulting from) their transfer from fresh water to seawater or salt water during their rearing.

Advantageously, the administration of insect powder to fish makes it possible to reduce their mortality during rearing by 5% with respect to the mortality of fish to which insect powder has not been administered.

By "administration" is meant the fact of making fish ingest food or feeding fish.

Preferably, the administration of insect powder allows fish mortality during rearing to be completely prevented.

More particularly, the administration of insect powder allows fish mortality following their transfer from fresh water to seawater during rearing to be completely prevented.

In fact, it has been shown that the mortality rate of fish fed with an insect powder is equal to 0% following their transfer from fresh water to salt water, such as for example 3 weeks after this transfer.

Conversely, the mortality rate of fish that have not been fed with an insect powder but with a fishmeal is equal to at least 5% following their transfer from fresh water to salt water, such as for example 3 weeks after this transfer.

The effect of the insect powder on the mortality of the fish during rearing is given in greater detail in Example 3 hereinafter.

Advantageously, the insect powder according to the invention comprises at least 67% by weight proteins and at least 0.1% by weight chitin, the percentages being given with respect to the total weight of insect powder.

By "proteins" is meant the quantity of crude proteins. The quantification of crude proteins is well known to a person skilled in the art. By way of example, the Dumas method or the Kjeldahl method may be mentioned. Preferably, the Dumas method, corresponding to the standard NF EN ISO 16634-1 (2008), is used.

Examples of such a powder are described in Examples 1 and 2 hereinafter.

Preferentially, the insect powder comprises 68% by weight crude proteins, more preferentially 70% by weight crude proteins, more preferentially 71% by weight crude proteins, the percentages by weight being given with respect to the total weight of insect powder.

According to the invention, by "chitin" is meant any type of chitinous derivative, i.e. polysaccharide derivative comprising N-acetyl-glucosamine units and D-glucosamine units, in particular the chitin-polypeptide copolymers (sometimes called "chitin-polypeptide composites"). These copolymers can also be combined with pigments, often of the melanin type.

Chitin is thought to be the second most-synthesized polymer in the living world, after cellulose. In fact, chitin is synthesized by numerous species in the living world: it partly constitutes the exoskeleton of crustaceans and insects, and the lateral wall which surrounds and protects fungi. More particularly, in insects, chitin thus constitutes 3 to 60% of their exoskeleton.

The determination of the chitin content is carried out by extraction thereof. Such a method can be the AOAC 991.43 method.

According to a first embodiment, the insect powder according to the invention comprises at least 67% by weight proteins and at least 5% by weight chitin, the percentages being given with respect to the total weight of insect powder.

Preferentially, this insect powder comprises between 5 and 16% by weight chitin, more preferentially between 8 and 14% chitin, the percentages by weight being given with respect to the total weight of insect powder.

Advantageously, this insect powder has an ash content less than or equal to 4% by weight with respect to the total weight of insect powder, and even more advantageously, less than or equal to 3.5%.

Ash constitutes the residue resulting from the combustion of the composition according to the invention.

The method for determining the ash content is well known to a person skilled in the art. Preferably, the ash was determined according to the method laid down by EC Regulation 152/2009 of 27 Jan. 2009.

The fat content of this insect powder is preferably comprised between 5 and 20% by weight with respect to the total weight of insect powder, more preferentially between 9 and 17%.

The methods for determining the fat content are well known to a person skilled in the art. By way of example and in a preferred manner, this content will be determined according to the method of EC Regulation 152/2009.

The terms "fat" and "lipids" are used interchangeably throughout the application.

Advantageously, the proteins of this insect powder have a digestibility greater than or equal to 70%, preferentially greater than or equal to 85% by weight with respect to the total weight of crude proteins.

The digestibility is a pepsin digestibility measured by the method described in Directive 72/199/EC.

More preferentially, the digestibility is greater than or equal to 86%, even more preferentially, greater than or equal to 88% by weight with respect to the total weight of crude proteins.

Advantageously, this insect powder according to the invention comprises between 35 and 65% by weight soluble proteins with respect to the total weight of proteins, and at least 50% of the soluble proteins have a size less than or equal to 12,400 g/mol.

By "total weight of proteins", is meant the weight of crude proteins present in the insect powder according to the invention.

By "soluble proteins" is meant, among the crude proteins, those which are soluble in an aqueous solution the pH of which is comprised between 6 and 8, advantageously between 7.2 and 7.6.

Preferably, the aqueous solution is a buffer solution the pH of which is comprised between 6 and 8, advantageously between 7.2 and 7.6. Preferentially, the buffer solution is an NaCl phosphate buffer solution, the pH of which is equal to 7.4+/−0.2.

Advantageously, this insect powder comprises between 38 and 60% by weight, preferably between 43 and 55% by weight soluble proteins with respect to the total weight of proteins.

Preferably, at least 60%, preferentially at least 70% of the soluble proteins have a size less than or equal to 12,400 g/mol.

More particularly, the soluble proteins have a size comprised between 6,500 and 12,400 g/mol.

Advantageously, less than 10%, preferably less than 8%, more preferentially less than 6% of soluble proteins have a size greater than or equal to 29,000 g/mol.

This insect powder can be prepared by a method comprising the following steps:
i) killing the insects,
ii) pressing the insects in order to obtain a press cake, and
iii) grinding the press cake.

The insects can be killed by scalding or blanching, as described in more detail hereinafter in Example 1.

Similarly, the pressing and grinding steps are described in more detail in this example.

Finally, the preparation method can also comprise a step of drying the press cake.

The drying step is advantageously carried out after the pressing step and before the grinding step, and is also described in more detail hereinafter in Example 1.

According to a second embodiment, the insect powder according to the invention comprises at least 71% by weight proteins and comprises between 0.1 and 2% by weight chitin, the percentages being given with respect to the total weight of insect powder.

Preferably, this insect powder has a protein content greater than or equal to 72% by weight, more preferentially greater than or equal to 74% by weight, even more preferentially greater than or equal to 75% by weight, with respect to the total dry weight of powder.

More particularly, this powder has a chitin content comprised between 0.5 and 3% by weight, more preferentially comprised between 0.8 and 2% by weight, even more preferentially comprised between 0.8 and 1.7% by weight with respect to the total dry weight of powder.

Preferably, this powder comprises between 5 and 20% by weight, preferably between 7 and 17% by weight lipids with respect to the total dry weight of powder.

More particularly, this powder comprises between 1 and 10% by weight, preferably between 2 and 6% by weight ash with respect to the total dry weight of powder.

Advantageously, the proteins of this insect powder have a digestibility greater than or equal to 70%, preferentially greater than or equal to 85% by weight with respect to the total weight of crude proteins.

More preferentially, the digestibility is greater than or equal to 88%, even more preferentially, greater than or equal to 92% by weight with respect to the total weight of crude proteins.

This insect powder can be prepared by a method comprising the following steps:
- killing the insects,
- separating the cuticles from the soft part of the insects,
- separating the soft part of the insects into a solid fraction, a fat fraction, and an aqueous fraction,
- drying the solid fraction in order to obtain a dry solid fraction,
- grinding the dry solid fraction in order to obtain an insect powder.

The insects can be killed by scalding or blanching, as described in more detail in Example 1 hereinafter.

The cuticle is the outer layer (or exoskeleton) secreted by the epidermis of the insects. It is generally formed of three layers: the epicuticle, the exocuticle and the endocuticle.

By "soft part" is meant the flesh (comprising in particular the muscles and the viscera) and the juice (comprising in particular the body fluids, water and haemolymph) of the insects. In particular, the soft part does not consist of the juice of the insects.

Separating the cuticles from the soft part of the insects can be carried out using a filter press or a belt separator.

By "belt separator" is meant a device that comprises a squeezing belt (belt press) and a perforated drum.

Advantageously, the insect powder according to the invention is obtained from an insect species belonging to the order of the Coleoptera, preferably from the species *Tenebrio molitor*, regardless of the embodiment of the invention. The insect powder according to the invention is then a beetle powder, preferably a powder of *Tenebrio molitor*.

The invention therefore relates more particularly to a beetle powder, preferably of *Tenebrio molitor*, for use thereof for the reduction of stress in fish during rearing, more particularly for the prevention or reduction of mortality of fish during rearing, in particular following their transfer from fresh water to seawater.

The invention further relates to the use of an insect powder for the prevention or reduction of stress in fish during their rearing.

More particularly, the invention relates to the use of an insect powder for the prevention or reduction of stress in fish following their transfer from fresh water to seawater during their rearing.

The invention further relates to the use of an insect powder for the prevention or reduction of mortality in fish during their rearing.

More particularly, the invention relates to the use of an insect powder for the prevention or reduction of mortality in fish following their transfer from fresh water to seawater during their rearing.

Thus, the insect powder is used, according to the invention, at least during the period of rearing fish in fresh water, i.e. before the transfer of the fish from fresh water to seawater.

Advantageously, this insect powder is also used to feed the fish following this transfer, preferably throughout the period of rearing.

The insect powder advantageously has the features described above.

The fish are advantageously the preferred fish described above.

The invention also relates to a method for rearing fish in which, during rearing, the fish are transferred from fresh water to salt water, and in which insect powder is administered to the fish in the 10 days preceding and/or in the 10 days following the transfer of the fish from fresh water to salt water.

The fish to which the rearing method according to the invention relates are the above-described preferred fish, and the insect powder advantageously has the features described above and in particular, the insect powder is advantageously a beetle powder, preferably a powder of *Tenebrio molitor*.

Preferably, the insect powder is administered in the 15 days, more preferentially in the 25 days, preceding the transfer of the fish.

Preferably, the insect powder is administered in the 15 days, more preferentially in the 25 days following the transfer of the fish.

Advantageously, the insect powder is administered in the days mentioned above preceding and following the transfer of the fish.

Advantageously, the insect powder is administered to the fish daily, preferably several times a day.

More particularly, the insect powder administered to the fish constitutes at least 5% by weight, preferably at least 10% by weight, preferentially at least 15% by weight, even more preferentially at least 20% by weight with respect to the total weight of their nutrition regime.

In the present application, by "nutrition regime" is meant all of the constituents administered to the fish, in given proportions, the constituents being able to be administered concomitantly or separately.

The invention also relates to a nutrition regime for fish, comprising at least 5% by weight, preferably at least 10% by weight, preferentially at least 15% by weight, even more preferentially at least 20% by weight insect powder with respect to the total weight of their nutrition regime.

The insect powder according to the invention can for example be used as an alternative to the fishmeal generally administered in the nutrition regime of fish. It may replace fishmeal partially or totally. Preferentially, the insect powder replaces fishmeal at 25% or more, by weight fishmeal, preferably 50% or more, by weight fishmeal.

Substitution of fishmeal by insect powder makes it possible to prevent or reduce stress, and more particularly mortality, of fish during rearing, in particular following their transfer from fresh water to seawater during rearing.

Preferentially, the insect powder replaces 50% of the fishmeal generally administered to fish.

The insect powder can also replace all of the fishmeal generally administered to fish.

Advantageously, the nutrition regime according to the invention comprises an insect powder comprising at least 71% by weight proteins and comprising between 0.1 and 2% by weight chitin, the percentages being given with respect to the total weight of insect powder.

The other constituents of the nutrition regime are advantageously selected from fishmeal, meal from soya, peas, wheat, maize, wheat gluten, maize gluten, concentrates from vegetable proteins such as soya, soya lecithin, oils (in particular fish, rapeseed), vitamins, minerals, antioxidants, natural food pigments in particular carotenoids such as astaxanthin, amino acids such as methionine, lysine, threonine, and/or food additives such as thickeners (guar gum), monosodium phosphate.

The vitamins and/or minerals can for example be added in the form of a premix.

The invention further relates to a method intended to prevent or reduce stress and more particularly to prevent or reduce the mortality of the fish during rearing, comprising the administration to fish of an insect powder.

The insect powder advantageously has the features described above.

The insect powder also makes it possible to promote or increase weight gain of the fish during rearing.

More particularly, the insect powder makes it possible for weight gain of the fish to be promoted or increased during the period of rearing the fish in fresh water, i.e. before the transfer of the fish from fresh water to seawater.

The effect of use of insect powder on the weight gain of the fish is shown in Example 3.

The invention also relates to the use of an insect powder comprising at least 67% by weight proteins and comprising at least 0.1% by weight chitin, the percentages being given with respect to the total weight of insect powder, as a nutrition supplement in fish nutrition.

The insect powder used as a nutrition supplement in fish nutrition can comprise at least 67% by weight proteins and at least 5% by weight chitin, the percentages being given with respect to the total weight of insect powder. This then is the insect powder of the first embodiment described above, including all the advantageous, particular and preferred features, and the method for obtaining it.

Alternatively, the insect powder used as a nutrition supplement in fish nutrition can comprise at least 71% by weight proteins and comprise between 0.1 and 2% by weight chitin, the percentages being given with respect to the total weight of insect powder. This then is the insect powder of the second embodiment described above, including all the advantageous, particular and preferred features, and the method for obtaining it.

The insect powder is advantageously a beetle powder, preferably a powder of *Tenebrio molitor*.

Other features and advantages of the invention will become apparent from the following examples, given by way of illustration.

FIG. 1 relates to the weights of the group "standard stress conditions" during the transfer from fresh water to seawater, corresponding to the fish receiving a nutrition regime chosen from three different diets comprising fishmeal replaced by 0% insect powder (100FM-0TMP, also called nutrition regime A), 50% insect powder (50FM-50TMP also called nutrition regime B) or 100% insect powder (0FM-100TMP also called nutrition regime C).

Figure 2:

FIG. 2 relates to the nutrition consumption of fish fed with a nutrition regime A, B, or C after transfer from fresh water to seawater.

EXAMPLE 1: METHOD FOR THE PREPARATION OF AN INSECT POWDER

The composition according to the invention is prepared from larvae of *Tenebrio molitor*. Upon receipt of the larvae, the latter can be stored at 4° C. for 0 to 15 days in their rearing tanks without major degradation before being killed. The weight of the larvae with respect to age of the larvae used is variable and as a result their composition can vary, as illustrated in Table 1 below:

TABLE 1

Biochemical composition of the larvae of *Tenebrio molitor* according to the weight thereof.

| | | Biomass (Insects) | | | | | |
|---|---|---|---|---|---|---|---|
| mg | | 23 | 35 | 58 | 80 | 108 | 154 |
| Dry matter | %* | 34 | 34 | 34.2 | 37.9 | 39.6 | 39.5 |
| Ash | %* | 1.59 | 1.52 | 1.6 | 1.75 | 1.67 | 1.43 |
| Crude proteins | %* | 22.6 | 22.2 | 22 | 23.2 | 23.1 | 23.2 |
| Lipids | %* | 6.62 | 6.88 | 7.98 | 10.3 | 10.9 | 11.7 |

*The % are expressed in dry weight with respect to the wet weight of larvae.

Step 1: Blanching the Insects

Living larvae (+4° C. to +25° C.) are conveyed in layers with a thickness comprised between 2 and 10 cm, on a perforated conveyor belt (1 mm) to a blanching chamber. The insects are thus blanched with steam (steam nozzles or bed) at 98° C. or with water at 100° C. (spray nozzles) or in mixed mode (water+steam). The residence time in the blanching chamber is comprised between 1 to 15 minutes, ideally 5 min.

The temperature of the larvae after blanching is comprised between 75° C. and 98° C.

Step 2: Pressing

Once blanched, the larvae are conveyed to the feed hopper of a continuous single-screw press. While passing into the press, the larvae are maintained at a temperature above 70° C. in order to increase the de-oiling yields. The principle of de-oiling is to pressurize the material inside a cylindrical cage by means of an arrangement of screws and rings arranged on the central shaft. The cage is lined inside with bars distributed in sections and kept apart by spaces of different thicknesses depending on the work area. The interstices thus arranged allow the flow of an oil fraction and limit the passage of the so-called "dry" matter, the protein fraction, which will be called "press cake", thus being involved in the pressurization.

The pressing yields obtained are comprised between 48 and 55%.

$$Y_{cake} = (\text{mass}_{cake}/\text{mass}_{juice} + \text{mass}_{cake})$$

The press cake obtained contains 35 to 40% dry matter, 67 to 75% proteins and 13 to 17% fats, the percentages by weight being given with respect to the dry weight of press cake.

Step 3: Drying

The press cake is then arranged on a tray in a thin layer (approximately 2 cm) and is dried in ventilated/stirred air at 90° C. for 5 hours in order to obtain a press cake having a dry matter content greater than 92%.

This step makes it possible to guard against any contamination having occurred since the killing.

The $a_w$ (water activity) after drying is 0.35. The microbiological results show an absence of *Salmonella* spp (method: IRIS *Salmonella* BKR 23/07-10/11) and Enterobacteria values less than 10 CFU/g (method: NF ISO 2128-2, December 2004, 30° C. and 37° C.).

Step 4: Grinding

The dried press cake, comprising mainly proteins, is finally ground using a continuous hammer mill (6 reversible moving parts—thickness 8 mm). The grinder is fed by a hopper with a flow rate control flap (180 kg/h). The perforated grill used to control the output granulometry is 0.8 mm. The speed of rotation of the motor is 3000 rpm (electric motorization, absorbed power 4 kW (5.5 HP)).

EXAMPLE 2: CHARACTERIZATION OF THE INSECT POWDER OBTAINED IN EXAMPLE 1

The insect powder prepared in Example 1 was characterized.

1. Analyses 1.1 Determination of the Moisture Content

The moisture content is determined according to the method originating from EC Regulation 152/2009 of 27 Jan. 2009 (103° C./4 h).

1.2 Determination of the Quantity of Crude Proteins

The crude proteins are determined according to the method called Dumas method, and corresponding to the standard NF EN ISO 16634-1 (2008).

1.3 Determination of the Quantity of Chitin

Dietary fibres from insect meal are essentially composed of chitin, the latter was therefore measured according to the AOAC 991.43 method. The values thus obtained are consequently slightly overestimated.

1.4 Determination of the Quantity of Fat

The fat was determined according to the method of EC Regulation 152/2009.

1.5 Determination of the Quantity of Ash

The crude ash was determined according to the method under EC Regulation 152/2009 of 27 Jan. 2009.

1.6 Determination of the Quantity of Phosphorus

The phosphorus is measured by ICP (induced coupled plasma) with internal calibration.

1.7 Determination of Energy

The energy value is obtained with the coefficients of EU Regulation 1169/201.

1.8 Determination of the Quantities of Amino Acids and Fatty Acids

This determination was carried out by gas chromatography after hydrolysis and derivatization of the amino acids and fatty acids respectively.

1.9 Determination of Pepsin Digestibility

The pepsin digestibility is measured by the method described in Directive 72/199/EC.

2. Results

The insect powder is detailed in Table 2 hereinafter.

TABLE 2

| Composition of the insect powder | | |
|---|---|---|
| | Unit | Composition |
| Macronutrient | | |
| Moisture | %* | 5.32 |
| Protein | %* | 67.09 |
| Chitin | %* | 8.0 |
| Fat | %* | 13.6 |
| Ash | %* | 3.21 |
| Total phosphorus | %* | 0.75 |
| Energy | MJ/kg | 23.74 |
| Amino acids | | |
| Arginine | %* | 2.56 |
| Histidine | %* | 1.39 |
| Isoleucine | %* | 2.11 |
| Leucine | %* | 3.99 |

TABLE 2-continued

| Composition of the insect powder | | |
|---|---|---|
| | Unit | Composition |
| Lysine | %* | 3.32 |
| Threonine | %* | 1.87 |
| Valine | %* | 2.91 |
| Methionine | %* | 1.43 |
| Cysteine | %* | 0.63 |
| Phenylalanine | %* | 1.98 |
| Tyrosine | %* | 2.68 |
| Taurine | %* | 0.42 |
| Aspartic acid + asparagine | %* | 4.51 |
| Glutamic acid + glutamine | %* | 6.36 |
| Alanine | %* | 3.83 |
| Glycine | %* | 2.54 |
| Proline | %* | 3.18 |
| Serine | %* | 2.94 |
| Fatty acids | | |
| C12:0 | %* | 0.03 |
| C14:0 | %* | 0.22 |
| C15:0 | %* | 0.01 |
| C16:0 | %* | 1.33 |
| C16:1 | %* | 0.05 |
| C16:1n-7 | %* | 0.16 |
| C17:0 | %* | 0.02 |
| C17:1 | %* | 0.01 |
| C18:0 | %* | 0.35 |
| C18:1n-9 | %* | 3.03 |
| C18:1n-7 | %* | 0.04 |
| C18:2n-6 | %* | 2.96 |
| C18:2tn-6 | %* | 0.02 |
| C18:3n-3 | %* | 0.14 |
| C20:0 | %* | 0.02 |
| C20:1n-9 | %* | 0.01 |
| C20:2n-6 | %* | 0.01 |
| C22:0 | %* | 0.01 |

*Percentages by weight are expressed with respect to the total weight of powder composition.

Moreover, a pepsin digestibility of 90+/−2% is obtained.

EXAMPLE 3: THE EFFECT OF THE INSECT POWDER OBTAINED IN EXAMPLE 1 ON THE MORTALITY AND WEIGHT GAIN OF THE FISH

1. Material and Methods

Fish:

Atlantic Salmon having an initial weight of 60 grams.

Nutrition Regimes:

The fish receive a nutrition regime chosen from three different diets comprising fishmeal replaced by 0% insect powder (nutrition regime A or "diet A"), 50% insect powder (called nutrition regime B or "diet B") or 100% insect powder (nutrition regime C or "diet C").

These nutrition regimes are detailed hereinafter:

| | Diet A 0% TMP | Diet B 50% TMP | Diet C 100% TMP |
|---|---|---|---|
| Fishmeal | 20.00 | 10.00 | 0 |
| Insect meal | 0 | 10.00 | 20.00 |
| Wheat | 10.75 | 11.30 | 11.75 |
| Wheat gluten | 14.50 | 13.90 | 13.30 |
| Soya protein concentrate | 18.00 | 18.00 | 18.00 |
| Maize gluten | 8.00 | 8.00 | 8.00 |
| Soya lecithin | 1.00 | 1.00 | 1.00 |
| Mixture of oils | 20.00 | 19.60 | 19.30 |
| Pre-mix of minerals | 0.59 | 0.59 | 0.59 |
| Pre-mix of vitamins | 2.00 | 2.00 | 2.00 |

-continued

|  | Diet A<br>0% TMP | Diet B<br>50% TMP | Diet C<br>100% TMP |
|---|---|---|---|
| Monosodium phosphate | 2.50 | 2.50 | 2.50 |
| Carop. Pink (10% Astax) | 0.05 | 0.05 | 0.05 |
| DL-methionine | 0.60 | 0.75 | 0.90 |
| L- Lysine | 1.20 | 1.40 | 1.60 |
| Thr | 0 | 0.10 | 0.20 |
| Total | 100 | 100 | 100 |
| Calculated chemical composition in the nutrition (% in the diet) | | | |
| Proteins | 45.0 | 45.0 | 45.0 |
| Lipids | 24.0 | 24.0 | 24.0 |

* TMP = insect powder, (namely "*Tenebrio molitor* powder")
**Fishmeal: Norse-70 LT (producer: 600031 VEDDE AS), Blue Whiting 54.6 North East Atlantic Ocean Ja Nei, Byproduct NVG Herring 24 Norwegian Sea Ja, Byproduct Herring 13.1 Norwegian Sea Ja, Byproduct whitefish 4.4 Norwegian Sea Ja Nei, Byproduct Mackerel 2.8 North Sea Ja Nei, Byproduct whitefish 1.1 Norwegian Sea
*** Carop. Pink (10% Astax) = natural food pigment based on astaxanthin Rearing Conditions:
Fresh Water Period from 4 April to 29 April (12° C.):
The fish are reared in fresh water in three aquariums, using a continuous light in order to synchronize the smoltification (industry standard).
The rearing conditions are as follows:

| Aquariums | 500 L |
|---|---|
| $O_2$ outlet | 80-99% saturation |
| Water flow rate | 12 L/min |
| Water speed | 8.8 cm/s |
| Photoperiod | 24 h |
| Duration of feeds | 1 min |
| Time between feeds | 20 min |
| Number of feeds per day | 72 |
| Feeders | Automatic conveyor |
| Water temperature | 12° C. |

Seawater Period from 29 April to the Month of September (Temperature Identical to that of the Environment)
For each nutrition regime:
120 fish are transferred to three conical aquariums (40 fish per aquarium) under minimal stress conditions, and
120 fish are transferred to three conical aquariums (40 fish per aquarium) according to standard stress conditions (for example, standard stress conditions due to overpopulation)
The total number of conical aquariums is therefore 18, counting 6 aquariums per nutrition regime.
2. Results
2.1. Weight of the "Standard Stress Conditions" Group on Transfer from Fresh Water to Seawater
See FIG. 1.
*FM: Fishmeal
*TMP=Insect powder
2.2. Weight and Mortality of "Standard Stress Conditions" Group 3 Weeks after the Transfer from Fresh Water to Seawater

| Replacement of fishmeal by insect powder | Weight | Mortality |
|---|---|---|
| Diet A, 0% insect powder | 109.4 g | 6.7% |
| Diet B, 50% insect powder | 109.2 g | 0% |
| Diet C, 100% insect powder | 106.3 g | 0% |

2.3. Nutrition Consumption of the Fish after Transfer
See FIG. 2.
2.4. Weight 4 Months after the Transfer

|  | Standard stress group | Minimal stress group | Total |
|---|---|---|---|
| Number of fish | 39-45 | 10 | 49-55 |
| Diet A (control) | 283.3 g ab | 308.1 g a | 287.7 g b |
| Diet B | 289.9 g a | 351.4 g a | 301.1 g a |
| Diet C | 271.5 g b | 331.2 g a | 282.4 g b |

The invention claimed is:
1. A method for reducing mortality in fish belonging to family Salmonidae said method comprising:
 rearing a fish in fresh water;
 transferring said fish from fresh water to seawater or saltwater for continued rearing;
 wherein an effective amount of beetle powder is administered to said fish in the 10 days preceding and/or in the 10 days following said fish's transfer from fresh water to seawater or salt water.
2. The method according to claim 1, wherein the fish belonging to the family Salmonidae is from the genus *Salmo, Salvelinus, Onchorynchus*, and/or *Hucho*.
3. The method according to claim 2, wherein the fish is selected from the following species:
 *Salmo salar, Salmo trutta, Oncorhynchus kisutch, Oncorhynchus tshawytscha, Oncorhynchus mykiss*, and *Salvelinus alpinus*.
4. The method according to claim 1, wherein said beetle powder comprises at least 67% by weight proteins and at least 0.1% A by weight chitin, the percentages being given with respect to the total weight of the beetle powder.
5. The method according to claim 4, wherein said beetle powder comprises at least 67% by weight proteins and at least 5% by weight chitin, the percentages being given with respect to the total weight of the beetle powder.
6. The method according to claim 4, wherein said beetle powder comprises at least 71% A by weight proteins and 0.1 and 2% by weight chitin, the percentages being given with respect to the total weight of the beetle powder.
7. The method according to claim 1, wherein said beetle powder is obtained from the species *Tenebrio molitor*.
8. The method according to claim 1, wherein said beetle powder is administered to the fish daily.
9. The method according to claim 1, wherein the beetle powder administered to the fish constitute at least 5% by weight with respect to the total weight of their nutrition regime.

* * * * *